US009208266B2

(12) United States Patent
Kriz et al.

(10) Patent No.: US 9,208,266 B2
(45) Date of Patent: Dec. 8, 2015

(54) PROPERTY PREDICTION FOR ASPHALTS FROM BLENDED SOURCES

(71) Applicant: ExxonMobil Research and Engineering Company, Annandale, NJ (US)

(72) Inventors: Pavel Kriz, Sarnia (CA); Lyle Edwin Moran, Sarnia (CA); John H. Brownie, Brights Grove (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 357 days.

(21) Appl. No.: 13/723,399

(22) Filed: Dec. 21, 2012

(65) Prior Publication Data

US 2014/0180650 A1    Jun. 26, 2014

(51) Int. Cl.
   *C10C 3/00*      (2006.01)
   *G06F 17/50*     (2006.01)
   *C08L 95/00*     (2006.01)
   *G01N 11/00*     (2006.01)
   *G01N 33/42*     (2006.01)

(52) U.S. Cl.
   CPC ............ *G06F 17/5009* (2013.01); *C10C 3/002* (2013.01); *C08L 95/00* (2013.01); *C10C 3/00* (2013.01); *G01N 11/00* (2013.01); *G01N 33/42* (2013.01)

(58) Field of Classification Search
   None
   See application file for complete search history.

(56) References Cited

U.S. PATENT DOCUMENTS

| | | | | |
|---|---|---|---|---|
| 3,939,004 A | * | 2/1976 | Corbett | 106/273.1 |
| 3,940,281 A | * | 2/1976 | Corbett | 106/278 |
| 5,109,041 A | * | 4/1992 | Matsuno et al. | 524/62 |
| 6,699,385 B2 | * | 3/2004 | Miller | 208/27 |
| 2007/0209967 A1 | * | 9/2007 | Allinson et al. | 208/58 |
| 2010/0081590 A1 | * | 4/2010 | Rosenbaum et al. | 508/110 |
| 2015/0191598 A1 | * | 7/2015 | Sirota | |

FOREIGN PATENT DOCUMENTS

EP       2071329 A2    6/2009

OTHER PUBLICATIONS

R. P. Sutton, D. F. Bergman, "Application of the Bergman-Sutton Method for Determining Blend Viscosity" p. 106-124, 2009.*
D. C. Villalanti, J. C. Raia, and J. B. Maynard, "High-Temperature Simulated Distillation Application in Petroleum Characterization", pp. 1-15, 2000.*
M.arrufet, A. Setiadarma, "Relaible heavy oil-solvent viscosity mixing rules for viscosities up to 450k, oil-solvent viscosity ratioes up to $4 \times 10^5$, and any solvent proportion" pp. 65-79, 2003.*

(Continued)

*Primary Examiner* — Kibrom K Gebresilassie
(74) *Attorney, Agent, or Firm* — Robert A. Migliorini

(57) ABSTRACT

Methods are provided for predicting the properties of an asphalt fraction that contains two or more asphalt components based on measurements of the viscosity for the asphalt fraction. Based on the measured viscosity, a virtual cut point is determined for a virtual asphalt blend that has the same viscosity (to within a tolerance value) as the measured viscosity for the asphalt fraction. The virtual cut point is then used to determine a variety of predicted property values for the asphalt fraction. Optionally, the predicted property values can be used to adjust the actual cut point for the distillation or separation process used for forming the asphalt fraction.

19 Claims, 4 Drawing Sheets

(56) References Cited

OTHER PUBLICATIONS

J. Al-Besharah, O. A. Salma, and S. A. Akashah, "Viscosity of Crude Oil Blends" pp. 2445-2449, 1987.*

"Overview of Crude Units" pp. 1-35, Apr. 3, 2007.*

The International Search Report and Written Opinion of PCT/US2013/070653 dated Mar. 25, 2014.

Wang et al., "Predicting saturates of sour vacuum gas oil using artificial neural networks and genetic algorithms," Expert Systems with Applications, 2010, vol. 37, pp. 4768-4771.

Han et al., "Approaches to predict viscosities of crude oil blends," Journal of Central South University of Technology, 2007, vol. 14, No. 1, pp. 466-470.

Sutton et al., "Application of the Bergman-Sutton Method for Determining Blend Viscosity," SPE Production & Operations, 2012, vol. 27, No. 1, pp. 106-124.

* cited by examiner

| crude | resid, yi (Tc=717.83K) | LN(KV135) (Tc=717.83K) | LN(HTPG), K | LTPG, K |
|---|---|---|---|---|
| Alpha | 0.8048 | 5.8 | 5.82 | 242.6 |
| Bravo | 0.0213 | 2.0 | 5.61 | 218.6 |
| Gamma | 0.0197 | 3.7 | 5.70 | 227.9 |
| Delta | 0.1543 | 5.7 | 5.80 | 251.8 |

PROPERTY PREDICTION FOR ASPHALTS FROM BLENDED SOURCES

FIELD

Methods are provided for predicting properties for asphalts formed from blends of feedstocks.

BACKGROUND

Asphalt is one of the world's oldest engineering materials, having been used since the beginning of civilization. Asphalt is a strong, versatile and chemical-resistant binding material that adapts itself to a variety of uses. For example, asphalt is used to bind crushed stone and gravel into firm tough surfaces for roads, streets, and airport runways. Asphalt, also known as pitch, can be obtained from either natural deposits, or as a by-product of the petroleum industry. Natural asphalts were extensively used until the early 1900s. The discovery of refining asphalt from crude petroleum and the increasing popularity of the automobile served to greatly expand the asphalt industry. Modern petroleum asphalt has the same durable qualities as naturally occurring asphalt, with the added advantage of being refined to a uniform condition substantially free of organic and mineral impurities.

The raw material used in modern asphalt manufacturing is petroleum, which is naturally occurring liquid bitumen. Asphalt is a natural constituent of petroleum, and there are crude oils that are almost entirely asphalt. The crude petroleum is separated into its various fractions through a distillation process. After separation, these fractions are further refined into other products such as asphalt, paraffin, gasoline, naphtha, lubricating oil, kerosene and diesel oil. Since asphalt is the base or heavy constituent of crude petroleum, it does not evaporate or boil off during the distillation process. Asphalt is essentially the heavy residue of the oil refining process.

Because asphalt is a residue from an oil refining process, if a blend of oils from more than one crude source is used as an input, the resulting asphalt residue will also represent a combination of the oils. Due to lower reliability of resulting asphalt quality prediction, proportions of individual crudes in the slate cannot be economized and a quality buffer is typically required. In the other words, a blend of feeds is selected that is conservative on quality, such as by using a higher percentage of heavy asphaltic feeds than is strictly needed, in order to increase the likelihood of meeting the asphalts specifications after manufacturing is done. However, having to select a heavier blend of feeds to form a desired asphalt can cause difficulties in other parts of a refinery, as using the heavier crudes that typically produce higher quality asphalt can limit the distillation throughput for the refinery.

Although individual asphalts can be characterized relative to a cut point temperature for separating heavy oil from the asphalt residue, conventional methods of characterizing blends of asphalts have been only partially successful. As a result, when a blend of oils is used to form an asphalt, the asphalt is usually characterized experimentally to determine all or nearly all specifications that determine the suitability of an asphalt for various potential uses. During this characterization time, storage tanks or another means for holding the asphalt prior to sale are required. If sufficient storage is not available, it may result in the slowing or even stopping of one or more additional refinery processes until the asphalt can be characterized and assigned a grade for sale.

SUMMARY

In an aspect, a method for predicting asphalt properties is provided. The method includes measuring a kinematic viscosity of an asphalt fraction at a temperature of 100° C. to 150° C., the asphalt fraction being formed by separation of a feed containing asphalt components from a plurality of crude sources based on a cut point temperature, the asphalt components being present in the feed in a first set of ratios; determining a virtual cut point for a virtual asphalt blend comprising the asphalt components having a kinematic viscosity that is within a viscosity tolerance of the measured kinematic viscosity, the virtual cut point being determined based on measured kinematic viscosity values for the asphalt components and the first set of ratios for the asphalt components; calculating a second set of ratios corresponding to a virtual composition of the asphalt components in the virtual asphalt blend based on the virtual cut point; calculating one or more properties other than kinematic viscosity for the asphalt fraction based on the second set of ratios for the asphalt components and at least one of the virtual cut point, the measured kinematic viscosity, or the determined kinematic viscosity for the virtual asphalt blend; and modifying the cut point temperature for the separation based on a calculated value for at least one of the one or more properties other than kinematic viscosity.

In another aspect, a method for predicting asphalt properties is provided. The method includes obtaining kinematic viscosity values at a plurality of cut point temperatures for a plurality of asphalt components, each of the plurality of asphalt components corresponding to an asphalt fraction derived from a single crude source at an identified cut point; obtaining values for one or more additional properties for each of the plurality of asphalt components; obtaining values for kinematic viscosity and for the one or more additional properties for a plurality of asphalt fractions comprising asphalt components from two or more crude sources; constructing a predictive model that correlates a measured viscosity value with values for the one or more additional properties for an asphalt fraction comprising a plurality of asphalt components, the predictive model comprising parameters for the one or more additional properties for each asphalt component that are fit to the obtained values for the plurality of asphalt fractions comprising asphalt components from two or more crude sources; measuring a kinematic viscosity of a first asphalt fraction comprising at least two asphalt components at a temperature of 100° C. to 150° C., the first asphalt fraction being formed by separation of a feed containing the at least two asphalt components based on a cut point temperature, the at least two asphalt components being present in the feed in a first set of ratios; determining a virtual cut point for a virtual asphalt blend having a kinematic viscosity within a viscosity tolerance value of the measured kinematic viscosity for the first asphalt fraction, the virtual cut point being determined based on measured kinematic viscosity values for the at least two asphalt components and the first set of ratios for the at least two components; calculating a second set of ratios corresponding to a virtual composition of the asphalt components in the virtual asphalt blend based on the virtual cut point; and predicting one or more properties other than kinematic viscosity for the first asphalt fraction based on the constructed predictive model, the second set of ratios and at least one of the virtual cut point, the measured kinematic viscosity for the first asphalt fraction, or the determined kinematic viscosity for the virtual asphalt blend.

DETAILED DESCRIPTION

Figure 1:
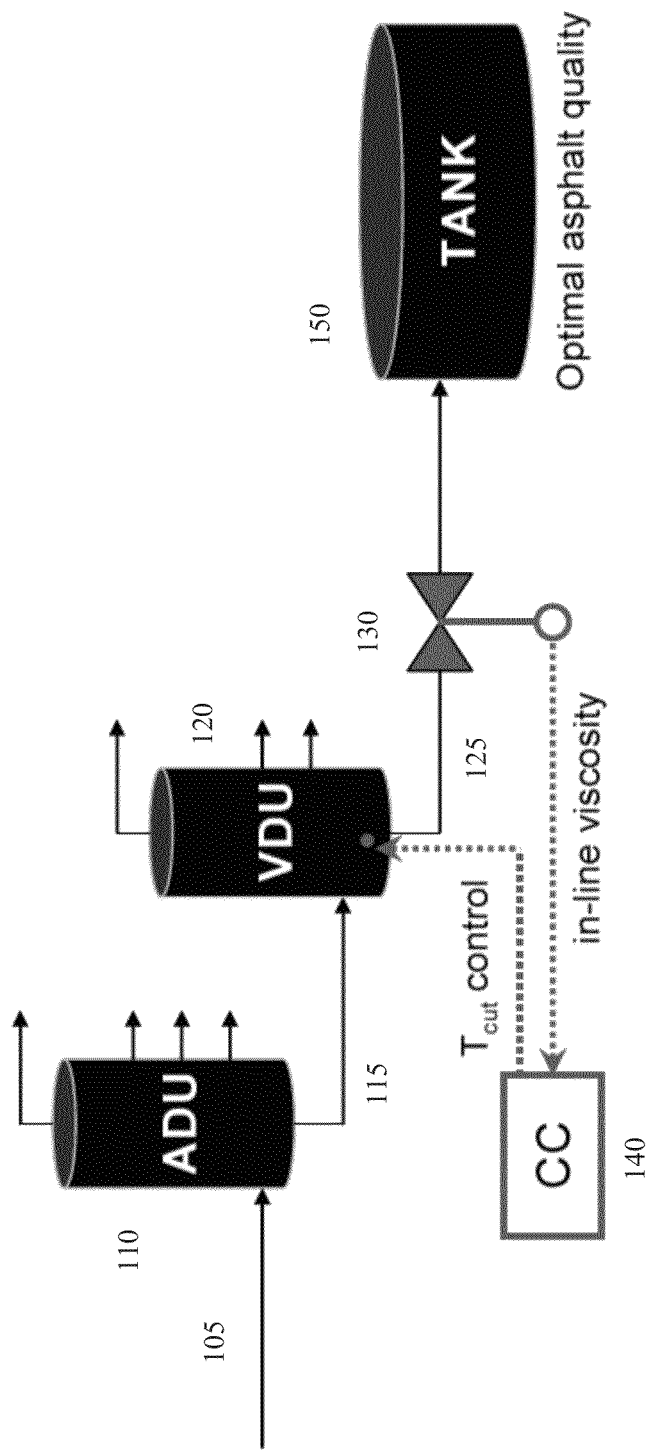
FIG. 1 shows an example of a refinery process flow that uses a predictive model according to the disclosure.

All numerical values within the detailed description and the claims herein are modified by "about" or "approximately" the indicated value, and take into account experimental error and variations that would be expected by a person having ordinary skill in the art.

Overview

In various aspects, methods are provided for predicting the properties of an asphalt fraction that contains two or more asphalt components based on measurements of the viscosity for the asphalt fraction. Based on the measured viscosity, a virtual cut point is determined for a virtual asphalt blend that has the same viscosity (to within a tolerance value) as the measured viscosity for the asphalt fraction. The virtual cut point is then used to determine a variety of predicted property values for the asphalt fraction. Optionally, the predicted property values can be used to adjust the actual cut point for the distillation or separation process used for forming the asphalt fraction. Adjusting the cut point for a distillation in real time can allow for production of an asphalt fraction with one or more desired property values that satisfy a specification without having to wait for laboratory based characterizations that require a longer time period to complete. Instead, a more limited set of characterizations can be used to confirm that an asphalt meets required specifications.

In various embodiments, a rheological/mathematical model can be developed based on at least the crude sources that will be used in a feed comprising components from a plurality of crude sources. The model can calculate or predict asphalt properties using only two inputs: on-line measured viscosity of the run-down and information regarding the slate of crudes that is used to form the feed that is then separated to form the asphalt fraction. Using the model can allow for real-time asphalt quality calculation at any stage of manufacturing. Calculated parameters consequently allow for immediate product release from a running tank; manufacturing optimization; in-line to truck/car blending; distillation operation; and crude slate optimization.

For lighter fractions derived from a crude oil, blending tools can often provide useful predictions the properties of blends containing components from a plurality of sources. This is in part due to the fact that lighter fractions have a relatively low number of distinct species. Additionally, blends of lighter fractions tend to have minimal amounts of non-linear interactions between components within the fractions. By contrast, the properties of a blend of asphalt fractions are difficult to predict based on a simple linear combination of individual asphalt fractions. The compositions of asphalt fractions often include a large number of species that may not be well understood. Additionally, due to the complexity of asphalt fractions, the plurality of asphalt fractions within a blend can have significant interactions, so that the properties of an asphalt blend do not correspond well to a simple linear combination of properties based on the cut point used to separate the blended asphalt from an original blended feed.

Preferably, the properties for an asphalt fraction containing multiple asphalt components can be predicted based on a readily available test that allows for derivation of the desired properties. In order to achieve this desired goal, a plurality of asphalt fractions derived from single crude sources can be characterized. The properties of these single crude asphalt fractions can be correlated with measured viscosities for the asphalts. A model can then be constructed based in part on the properties of the single source asphalt fractions.

In order to use the model, a viscosity measurement can be performed on a asphalt fraction derived from separation of a suitable feed at a suitable cut point. However, the cut point used for forming the asphalt fraction is not used to predict the properties of the asphalt fraction based on the model. Instead, the cut point profiles for each component in the feed for forming the asphalt fraction can be used to determine the viscosity that would be expected for a virtual asphalt blend based on a virtual cut point temperature. A virtual cut point is then calculated or selected so that the viscosity of the virtual asphalt blend matches the measured viscosity to within a tolerance amount. This virtual cut point and the corresponding virtual asphalt blend are then used as the basis for predicting the remaining properties for the blended asphalt.

In this discussion, reference will be made to crude sources, asphalt fractions, asphalt components, feed components, and virtual asphalt blends. An asphalt fraction represents an asphalt fraction made in any convenient manner, such as an asphalt fraction formed by distillation of a suitable feedstock at a suitable cut point temperature. An asphalt component is defined herein to refer to an asphalt fraction that is derived from a single crude source. Similarly, a feed component is defined herein as a portion of a feed that is derived from a single crude source. A crude source is defined herein as a combination of a) a source of oil, tar sands, or another type of petroleum that can be used to form a crude oil stream, and b) any processing that is used to form such a crude oil stream prior to distilling the crude oil stream to form the asphalt fraction. Thus, use of a different distillation cut point during asphalt formation does not impact the source of a crude oil stream. However, two crude oil streams extracted from the same location, but that undergo different processing and/or separation procedures prior to reaching a refinery could be considered as crude oil streams from different sources. A virtual asphalt blend refers to composition for an asphalt fraction that would be formed if a distillation of an existing asphalt fraction were performed at a virtual cut point, and if the distillation behaved in an idealized manner with respect to asphalt formation for individual asphalt components in the asphalt fraction. Virtual asphalt blends will be discussed in greater detail below.

It is noted that a distinction is made between the measured properties for an asphalt fraction and the properties of a virtual asphalt blend. An asphalt fraction represents an asphalt fraction formed from distillation or other separation of a feed. A virtual asphalt blend is a hypothetical asphalt composition that is calculated using a virtual cut point and based on characterization of the individual components in a feed. A virtual cut point is selected so that the calculated viscosity of a virtual asphalt blend is the same (within a tolerance) as the measured viscosity for a corresponding asphalt fraction. The virtual cut point will typically differ from the actual cut point used to make the corresponding asphalt fraction.

Asphalt Feedstocks

Some feedstocks in accordance with the present disclosure are heavy oils that include at least a portion of asphaltenes. Such heavy oils are suitable, possibly after additional distillation, for making an asphalt. Asphalt is a viscoelastic semi-solid bituminous material derived from the distillation residue of crude petroleum. Asphalt may be obtained from a variety of crude oil sources or fractions, including straight run vacuum residue, mixtures of vacuum residue with diluents such as vacuum tower wash oil, paraffin distillate, aromatic and naphthenic oils and mixtures thereof, oxidized vacuum residues or oxidized mixtures of vacuum residues and diluent oils and the like. Because it is hydrophobic and has good adhesive and weathering characteristics, asphalt is widely used as a binder or cement for stone or rock aggregate in pavement construction (typically only 5 wt % of the mixture). Other feedstocks suitable for use in the disclosure include whole or reduced petroleum crude oils, atmospheric residua feedstocks, and vacuum residua feedstocks.

One option for defining a boiling range is to use an initial boiling point for a feed and/or a final boiling point for a feed. Another option, which in some instances may provide a more representative description of a feed, is to characterize a feed based on the amount of the feed that boils at one or more temperatures. For example, a "T5" boiling point for a feed is defined as the temperature at which 5 wt % of the feed will boil. Similarly, a "T95" boiling is defined as the temperature at which 95 wt % of the feed will boil.

A typical feedstock for forming asphalt can have a normal atmospheric boiling point of at least 350° C., more typically at least 400° C., and will have a penetration range from 20 to 500 dmm at 25° C. (ASTM D-5). Alternatively, a feed may be characterized using a T5 boiling point, such as a feed with a T5 boiling point of at least 350° C., or at least 400° C., or at least 440° C.

Another example of a feedstock suitable for forming asphalt is a feedstock derived from an atmospheric resid fraction or a similar petroleum fraction. For example, when a whole crude oil, partial crude oil, or other feedstock is processed in a refinery, one common type of processing is to distill or fractionate the crude oil based on boiling point. One type of fractionation is atmospheric distillation, which can result in one or more fractions that boil at less than 650° F. (343° C.) or less than 700° F. (371° C.), and a bottoms fraction. This bottoms fraction corresponds to an atmospheric resid.

The bottoms fraction from atmospheric distillation can then be separated or fractionated using vacuum distillation. This generates one or more (vacuum) gas oil fractions and a vacuum resid fraction. Because the vacuum distillation is typically performed on a resid from atmospheric distillation, a vacuum gas oil fraction can be defined as a fraction with a T10 boiling point of at least 650° F. (343° C.), such as at least 700° F. (371° C.). Preferably, a vacuum gas oil fraction can have a T5 boiling point of at least 650° F., such as at least 700° F. The vacuum resid fraction may be suitable for use as an asphalt. The distillation cut point for forming the vacuum bottoms fraction can be selected based on a desired amount of vacuum gas oil and/or a desired quality for the asphalt fraction. Selecting a higher temperature cut point can increase the amount of a vacuum gas oil. However, such a higher temperature cut point will typically reduce the quality of the corresponding asphalt. Since both vacuum gas oil yield and asphalt quality are also dependent on the nature of the feedstock, the temperature cut point to achieve a desired combination of vacuum gas oil yield and asphalt quality will vary. A suitable cut point for the vacuum bottoms fraction to achieve a desired asphalt quality and/or to achieve a desired vacuum gas oil yield can be at least 750° F. (399° C.), such as at least 950° F. (510° C.) or at least 1050° F. (566° C.).

Determining Virtual Cut Point Based on Measured Viscosity

Performing a distillation on a feed containing multiple feed components will typically result in an asphalt fraction where the ratios of the various crude sources in the asphalt fraction will differ from the ratios of the various crude sources in the feed. This is due to the different boiling point profiles for each crude source in the slate used to form a feed. For example, consider a feed containing equal weights of components (i.e., a 1 to 1 ratio) from two crude sources. In this example, the first crude source has a lower temperature boiling point profile. When a distillation is performed on such a feed to generate, for example, a vacuum gas oil fraction and an asphalt fraction, the ratio of the first asphalt component to the second asphalt component in the asphalt fraction will typically be less than 1 to 1. However, due to interactions between components in a feed used to form an asphalt fraction, the exact ratio of asphalt components in the resulting asphalt is somewhat difficult to predict.

More generally, based on the actual cut point used for forming the vacuum gas oil and asphalt fractions, and the knowledge of the amount of each crude source in the original composition, it might be expected that the actual cut point could be used to determine the ratio of each crude source in the asphalt product. Further, it might be expected that such ratio information could be used to calculate an expected viscosity (or other expected properties) based on the viscosities (or other properties) for asphalts formed from the individual components at the actual cut point. Unfortunately, this type of calculation does not lead to an effective prediction of properties for an asphalt fraction containing multiple components.

One initial step in predicting the properties of an asphalt fractions is to characterize the properties of individual asphalt components in the asphalt fraction. This can represent testing performed specifically to develop the model or accumulated data from prior testing on asphalt fractions derived from single crude sources. The testing for asphalt fractions from individual crude sources will preferably include measurements for kinematic viscosity as well as any other property that is desired for prediction. The viscosity as well as the other properties are characterized for asphalt fractions formed using various cut point temperatures over a range of interest.

As noted above, using the actual cut point temperature used for forming an asphalt fraction does not result in a desired accuracy for property prediction. Instead of using the actual cut point temperature as a basis for predicting properties, the viscosity of an asphalt fraction can be measured. Preferably, the viscosity of the asphalt fraction is measured at a temperature where the asphalt behaves as a Netownian fluid. An example of a suitable temperature is 135° C. At 135° C., the viscosity of a wide variety of asphalt fractions can be measured while the asphalt is in a Newtonian fluid state. For asphalt fractions that have a high hardness value, it may be necessary to measure the viscosity at a higher temperature, such as up to 150° C. For many other types of asphalt fractions, a temperature of at least 100° C. is sufficient for the asphalt fraction to act as a Newtonian fluid.

The measured kinematic viscosity for the asphalt fraction can then be used to determine a "virtual" cut point. A virtual cut point represents a cut point temperature that produces a virtual asphalt blend that has a kinematic viscosity that matches the measured viscosity. The composition of the virtual asphalt blend is determined by using a virtual cut point temperature in combination with the ratios of the components in the feed for forming the actual asphalt fraction. For an individual feed component, the yield of asphalt for the feed component can be determined at a given cut point temperature. This allows for determination of a composition for a potential virtual asphalt blend. Based on viscosity data for asphalt components at a range of potential cut point temperatures, the viscosity that would be expected for an asphalt component at a given virtual cut point can be determined. The composition of the virtual asphalt blend can then be combined with the kinematic viscosity information to determine a viscosity for a virtual asphalt blend. Any convenient method can then be used to determine a virtual cut point temperature that would lead to a viscosity for the virtual asphalt blend that matches the measured viscosity for the asphalt fraction. For example, the virtual cut point temperature can be determined by successive approximations or by any other convenient method for using the single crude source viscosities and the original compositional slate to identify a virtual cut point temperature that matches the measured value to within a specified viscosity tolerance. Any convenient tolerance can be used for determining a match, such as less than 0.5 cSt, or less than 0.1 cSt, or less than 0.05 cSt, or less than 0.01 cSt.

Predicting Asphalt Properties Based on Viscosity (Via a Virtual Cut Point)

As described above, a measured viscosity at a temperature where the asphalt components of the asphalt fraction are in a Newtonian fluid state can be used to derive a virtual cut point temperature. The virtual cut point temperature can then be used as the basis for predicting properties of the asphalt fraction. To determine properties, a composition for a virtual asphalt blend is determined that corresponds to separation of the feed at the virtual cut point temperature. The composition for the virtual asphalt blend based on the virtual cut point is then used to calculate other properties of interest for the virtual asphalt blend. For each property, a weighted average of the properties of the individual crude sources is formed. This weighted average is based on compositional weights percentages in the virtual asphalt blend as determined by the virtual cut point. The weighted average can correspond to a linear weighted average for a property, a weighted average of the log values of the property, or another convenient type of weighted average based on the compositional weight percentages in the virtual asphalt blend. The high temperature performance grade value is an example of a property where a weighted average of the log values of a property can be used.

In an embodiment, the properties for the virtual asphalt blend can be used directly as the predicted properties for the asphalt fraction. However, directly using the properties calculated for the virtual asphalt blend will likely result in some residual errors relative to the actual properties of an asphalt fraction. The predicted values for the asphalt fraction can be improved by including a set of fit parameters in the predictive model. For example, a set of fit parameters can be used that provide an extra degree of freedom for each asphalt component. This extra degree of freedom represents a variable that can be fit based on historical data from measurements of asphalt fractions derived from single crude source and/or data from measurements of asphalt fractions containing a plurality of asphalt components. The variables can be fit to the historical data by any convenient method, such as least squares.

Depending on the embodiment, various properties for an asphalt fraction may be of interest. Examples of properties include high temperature performance grade (HTPG) and low temperature performance grade (LTPG); dynamic shear rheometer test values, such as pressure aging vessel residue; bending beam rheometer values, such as n value or stiffness; penetration; and absolute viscosity at various temperatures, such as 60° C.

Real Time Process Feedback

One option for using the model described above is to use the model to provide real-time feedback for an asphalt formation process. One advantage of using the viscosity at a temperature between 100° C. and 150° C. as the measured property is that a viscosity can be obtained in a relatively short time with an in-line monitor. Thus, a viscosity can be obtained at a convenient interval, such as once a minute. Because an asphalt fraction will often be at a higher temperature than the desired temperature for the viscosity measurement, a slip stream of the asphalt fraction can be withdrawn and cooled in order to obtain the viscosity measurements.

By obtaining a measured viscosity at a convenient time interval, the properties for the resulting asphalt fraction can be predicted during the distillation or separation for forming the asphalt fraction. If one or more of the predicted properties is outside of a desired range, the actual cut point (or other control variable) for the separation to form the asphalt fraction can be modified in order to achieve the desired property value.

FIG. 1 shows a schematic example of a refinery configuration for using a viscosity based predictive model to provide real time feedback for asphalt formation. In FIG. 1, an initial atmospheric distillation 110 is performed on a feed 105 that includes portions or components from at least two crude sources. The bottoms 115 from atmospheric distillation 110 are then separated using a vacuum distillation unit 120. A selected cut point is used to separate the (bottoms) asphalt fraction 125 from the next highest boiling fraction generated by the vacuum distillation unit 120. The viscosity of the asphalt fraction 125 is measured using an in-line viscosity analyzer 130, which may optionally analyze the viscosity of a slip stream (not shown) of the asphalt fraction 125. Such viscosity measurements can be performed at any convenient time interval, such as once per minute. The information from viscosity analyzer 130 is fed back to a general purpose computer or other processor 140 that can use the predictive model. Based on the measured viscosity, the properties of the asphalt fraction 125 are predicted. If the predicted properties do not match desired specifications, the processor 140 can adjust the cut point being used in vacuum distillation unit 120. This allows an asphalt fraction 125 with desired properties to be made and stored in tank 150 without having to wait for a day or longer to obtain other types of laboratory analysis of the asphalt fraction 125.

It is noted that the real-time feedback method described above can also be used for forming an asphalt from a single crude source. In such an embodiment, data can be accumulated that correlates viscosity with other properties for a crude source. When an asphalt is made from a feed corresponding to the crude source, the viscosity analyzer can be used to the properties for the asphalt based on the current measured viscosity. The actual cut point can then be modified based on the apparent cut point that corresponds to the measured viscosity.

Predictive Model Refinements

As noted above, the model can include a parameter for each crude property value that is fit to historical data. Because the historical data can include measurements on both single source asphalt fractions and asphalt fractions containing multiple components, the fit parameters can provide some representation of the individual asphalt components. However, it is more difficult to capture interactions between a given pair of asphalt components when the asphalt components are present in the same asphalt fraction. To reflect the interactions between particular asphalt components, additional non-linear blending coefficients can be added to the model for each pair of asphalt components where sufficient historical data is available. If the historical data provides only a limited number of examples for a given pair of asphalt components in asphalt fractions, using non-linear blending coefficients may lead to underdetermined coefficients. However, where the historical data provides a sufficient number of data points, the additional blending coefficients for pairs of asphalt components can be used to modify the weight given to the values for the pair of asphalt components. It is noted that coefficients can be used in situations where coefficients are not available for all potential pairs in an asphalt fraction.

Another potential modification is to continue to update the model over time. As noted above, a variety of fit parameters or coefficients are present within the model. These parameters are fit based on historical data for asphalt fractions from individual crude sources as well as asphalt fractions containing a plurality of asphalt components. However, individual crude sources can also change over time, such as due to changes in the composition of the actual crude source or changes in how the crude source is extracted and/or preprocessed at the source. To reflect such changes, the fit parameters in the model can continue to be updated as more data becomes available. Additionally, as time passes, data that is sufficiently old can either be given a reduced weight during the fitting procedure or even omitted entirely.

Still another potential modification is to expand a model to incorporate data from multiple refineries that have formed asphalt fractions from a given crude source. In some embodiments, the data in the model can be based on forming asphalt fractions at a single refinery from various crude sources. However, data from multiple refineries can be incorporated into a single model if desired. The data from each refinery can be given the same weight, or the data can be weighted based on the refinery the model is being used at, so that historical data from the refinery currently making a prediction is given greater weight than data from other refineries. Incorporating data from multiple refineries can allow information a given crude source and/or interactions of pairs of crudes to be built up in a more rapid manner.

Figure 2:
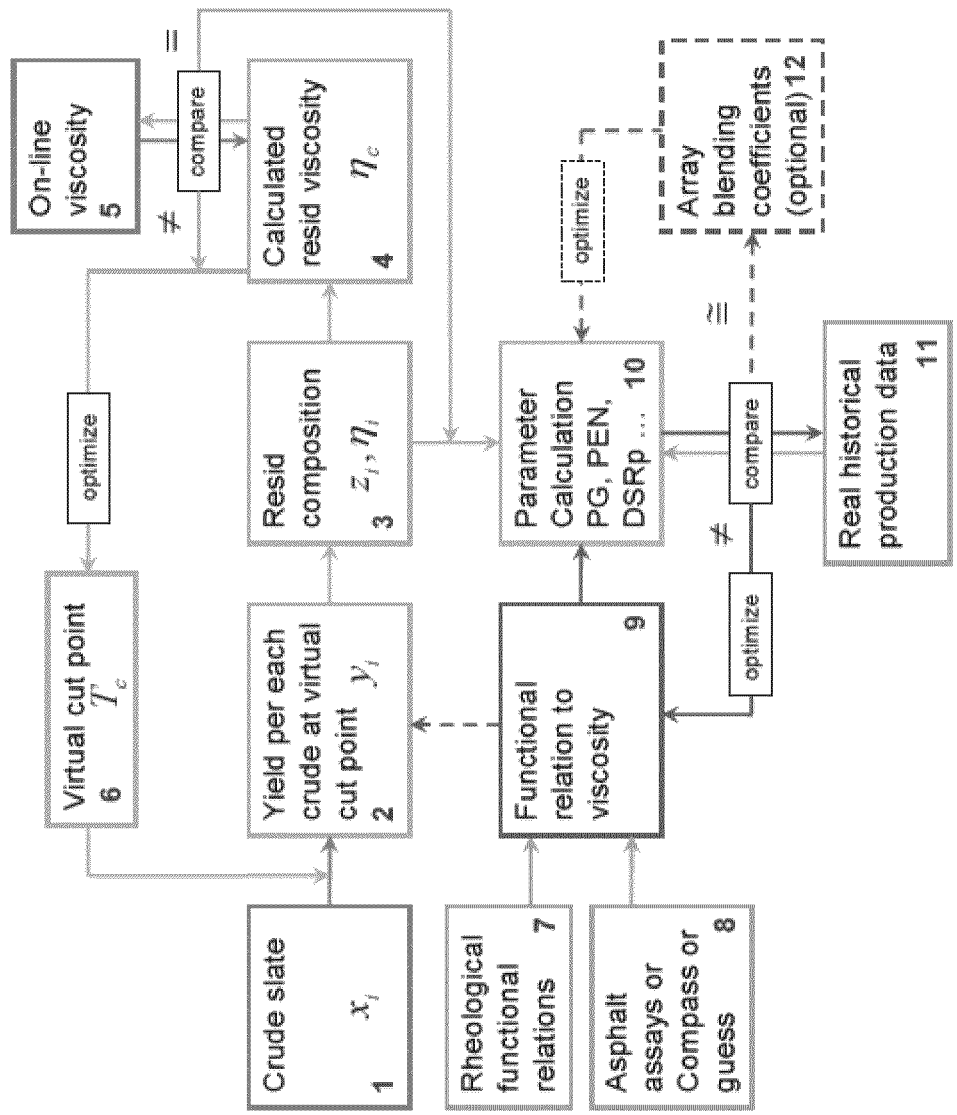
FIG. 2 shows a flowchart of creating a predictive model for properties of asphalt blends according to an embodiment of the disclosure.

FIG. 2 shows an example of constructing a predictive model that includes at least some of the model refinements described above. In FIG. 2, a crude slate 1 specifies a type and amount for a plurality of components that are included in a feed for forming an asphalt fraction. Based on a virtual cut point 6, a yield 2 for each of the feed components within a virtual asphalt blend is determined. The yield values combined with the crude slate composition can be used to determine a virtual composition 3 for the virtual asphalt blend corresponding to the virtual cut point. A calculated viscosity 4 for the virtual asphalt blend can then be determined. This calculated viscosity can be compared with a measurement 5 of the viscosity for the actual blended asphalt. If the calculated viscosity 4 and the measured viscosity 5 do not match to within a tolerance value, a new virtual cut point is selected and calculations 2-4 are repeated. When a virtual cut point 6 is selected that causes the calculated viscosity 4 for the virtual asphalt blend to match the measured viscosity 5, the virtual composition 3 corresponding to the virtual asphalt blend can be used to predict properties 10 for the blended asphalt. The property predictions 10 are based on measured viscosity values for the asphalt components within the feed as well as correlations 9 between measured viscosities and other measured properties 8. The model can be further improved by using historical data 11 to fit additional parameters for the properties in the model. Optionally, a second group of blending coefficients 12 can be fit to capture interactions between asphalt components that are used together frequently as components within a feed.

Applications for Predictive Model

The ability to predict properties for an asphalt fraction containing multiple asphalt components based on a kinematic viscosity measurement allows the predictive model to be applied for a variety of applications. In one example, the on-line measured viscosity and information a crude slate are fed into the predictive model in real-time. The model is able to work with a constant or a dynamically changing crude slate. Viscosity of the product in the run-down tank is calculated from viscosity, production time, and production rate data. Product specification parameters can be calculated in real time for the run-down tank. This can allow the product to be released to sales immediately, i.e. from the live tank, so that the tank is open to production and sales at the same time. In another version of this scenario, the tank can be filled and closed for production and asphalt viscosity can be verified by QA lab and used for product early release.

In another example, the crude slate information and one or more target product properties can be fed into predictive model. The crude slate can be constant or dynamically changing over the production time. The predictive model can calculate all remaining asphalt properties including the target viscosity. The cut point for the vacuum distillation unit can then be changed to adjust the run-down viscosity—as provided in real-time mode by the rundown viscosity analyzer. Another option is to use the predictive model in fully predictive mode. In this option, desired product property(ies) are specified and the optimal crude weight fractions, target viscosity, and any other desired product specification parameters are calculated.

Still another option is to use the predictive model to calculate the most suitable and/or economical crude slate. A number of available crudes can be selected. One or more target asphalt properties can also be specified. Optionally, limits on the weight fraction of each component can also be specified. The predictive model can then be used to calculate the weight fraction in order to meet the suggested requirements. The predictive model can also be used to maximize a component crude for a given slate (for instance the cheapest) or minimize a component crude for a given slate (for instance minimizing the heaviest component to enhance throughput).

Still another option is to use the predictive model to effectively remove the intermediate product tankage from service. Instead, the predictive model can allow in-line blending of the intermediate product directly to a car or tank truck.

Yet another option is to use the predictive model to dynamically calculate the target blend ratio and viscosity using crude slate information, the actual viscosity of all components, and the target properties of the blend. The predictive model can control the quality of the blended product based on its viscosity, thus allowing for immediate product release.

EXAMPLES

The following is an example of using a rheological model to predict properties of a blended asphalt product. In this example, a feed including components from four different crude sources was separated at a cut point to form at least one gas oil fraction and an asphalt fraction. Each of the feed components represents a component from a crude source that had been previously characterized with regard to asphalt fraction formation. As a result, properties for asphalt fractions derived from each crude source at a range of cut point temperatures are available in the model database. It is noted that although generic names were assigned to the crude sources, this example represents a working example based on fitting of a model to historical data followed by measuring a viscosity for an asphalt fraction derived by distilling a feed composed of four different components.

Figure 3:
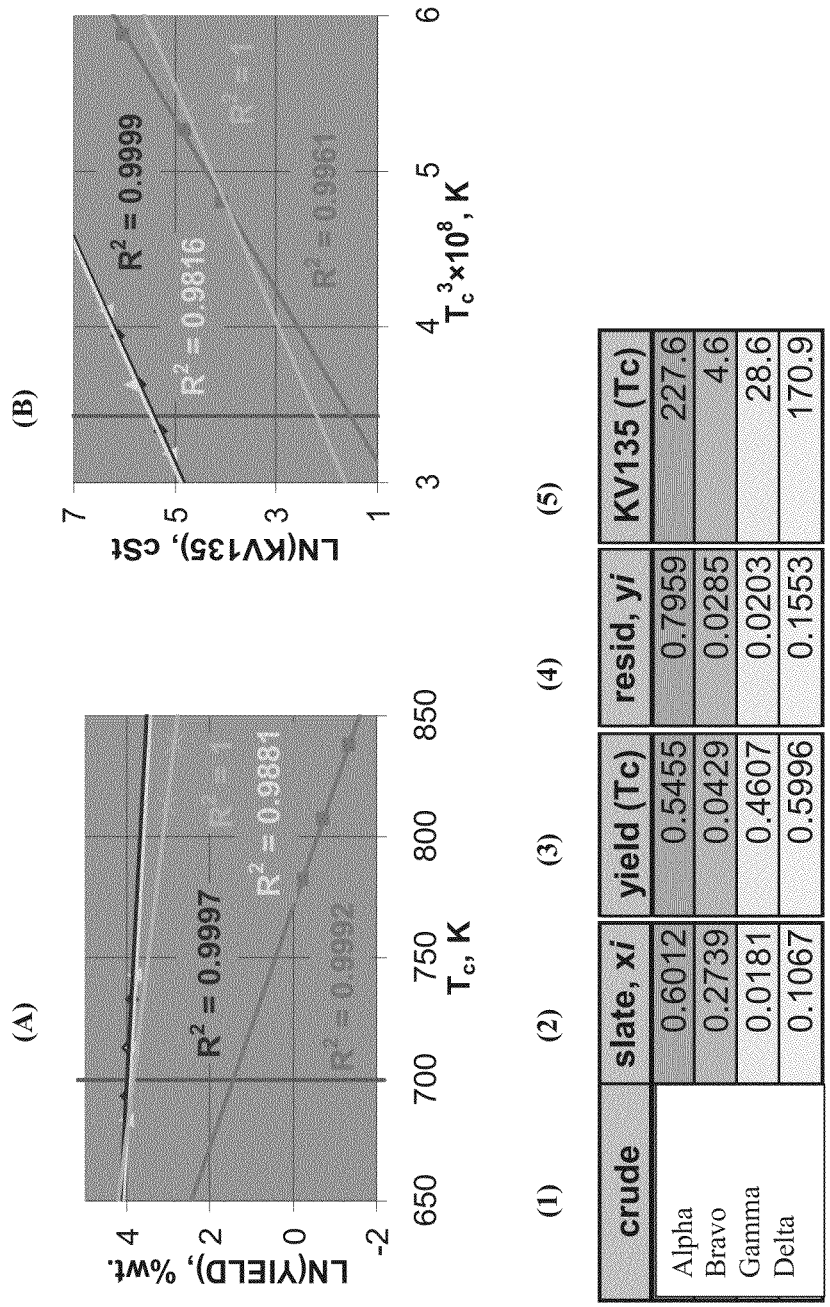
FIG. 3 shows an example of a virtual cut point determination according to an embodiment of the disclosure.

In this example, the identities of the crudes in the feedstock for asphalt formation are shown in column (1) of FIG. 3. The identities correspond to the source of each crude that is included in a feed for forming an asphalt fraction. Column (2) in FIG. 3 shows the amount (weight percent) of each crude present in the feed for forming the asphalt fraction. A distillation is then performed to form an asphalt fraction. It is noted that the actual cut point temperature used for the distillation is not needed to apply the predictive model.

After performing the distillation, the viscosity of the resulting asphalt fraction is measured, such as by measuring the kinematic viscosity at 135° C. In this example, the measured viscosity at 135° C. for the resulting asphalt fraction is 286.0 cSt. This measured viscosity can then be used to identify a virtual cut point for a virtual asphalt blend that would have the same viscosity as the measured viscosity. One method for determining the virtual cut point is to construct plots similar to plots (A) and (B) shown in FIG. 3. Plot (A) is a log plot of the yield of asphalt formed from each component in the feed as a function of temperature. In other words, plot (A) in FIG. 3 shows the wt % for each of the four feed components that will remain in an asphalt fraction after distillation as a function of cut point temperature. For example, column (3) in FIG. 3 shows the wt % that will remain in an asphalt fraction for each feed component at a virtual cut point temperature of 700° K. The 700° K value for the virtual cut point represents an initial guess for the virtual cut point. As shown in column (3), feed components Alpha, Gamma, and Delta contribute between 46% and 60% of their original feed amount to the resulting asphalt fraction. By contrast, at a cut point of 700° K, less than 5% of feed component Bravo remains in the asphalt fraction.

The yield for each feed component in a resulting asphalt fraction from plot (A), as shown in column (3), can then be multiplied by the initial weight percentage of each component in the feed, as shown in column (2). This produces a net yield for each component in the feed in a virtual asphalt blend. The net yields can then be normalized so that the sum of the net yields in the virtual asphalt blend is 1. This provides the weight percent of each feed component that would be present in a virtual asphalt blend based on the virtual cut point. The composition of the virtual asphalt blend is shown in column (4). It is noted that the actual yield, both of individual asphalt components and overall yield, is likely to differ from the yields for the components in the virtual blended asphalt (to the degree such yields can be determined for the asphalt fraction).

The values in column (4) can then be used in conjunction with plot (B) in FIG. 3 to determine a viscosity for the virtual asphalt blend. Plot (B) in FIG. 3 shows a plot of the log value of the measured viscosity at the measurement temperature (such as 135° C.) for asphalts derived from each crude source versus the cube of the cut point temperature used to form an asphalt. Based on this plot, the viscosity value for an asphalt fraction derived from each individual crude source at the virtual cut point temperature can be determined. In column (5), the viscosity at a virtual cut point temperature of 700° K is shown for each component. The compositional weights for the virtual asphalt blend in column (4) can then be multiplied by the viscosity for each component in column (5), and these values can be added together to generate a viscosity for the virtual asphalt blend at a virtual cut point temperature of 700° K. Based on the values in columns (4) and (5), the viscosity of the virtual asphalt blend at 700° K is 186.8 cSt. This is substantially lower than the measured viscosity for the actual asphalt fraction of 286.0 cSt.

Based on the shapes of the distillation curves and the viscosity versus temperature curves for the individual components, it appears that the virtual cut point temperature is higher than 700° K. In this example, additional estimates for the virtual cut point were made until a viscosity for the virtual asphalt blend was found that differed from the measured viscosity value by less than a tolerance amount. In this example, it was determined that a virtual cut point of 717.83° K resulted in a virtual asphalt blend with a viscosity that matches the measured value of 286.0 cSt to within a convenient tolerance value, such as within 0.05 cSt or less, and preferably within 0.02 cSt or less.

After determining the virtual cut point, the composition for the virtual asphalt blend corresponding to the virtual cut point can be determined using the values in column (2) and plots (A) and (B) of FIG. 1, as described above. The normalized composition weights for the virtual asphalt blend at the virtual cut point of 717.83° K are shown in column (6) of FIG. 4. Based on the virtual cut point, the viscosity at 135° C. for each component in the asphalt blend can also be determined. The logs of these viscosity values are shown in column (7) of FIG. 4. The values in columns (6) and (7) can then be used to determine various properties for the virtual asphalt blend that can be used as predictions for the properties of the blended asphalt, optionally as modified by additional fit parameters in the model.

Figure 4:
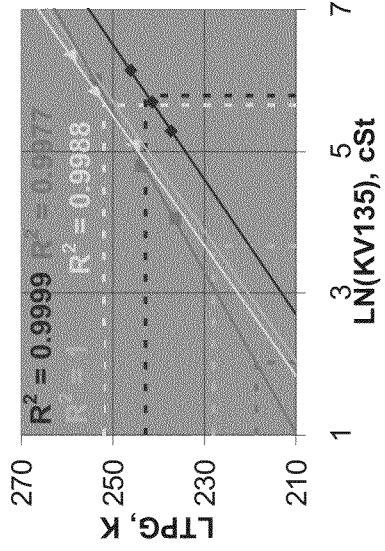
FIG. 4 shows an example of property prediction according to an embodiment of the disclosure.
Figure 4:
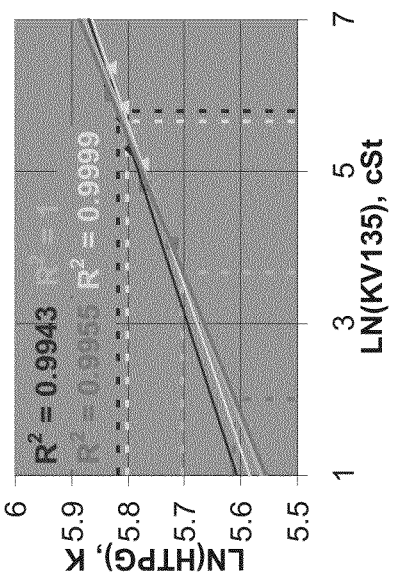

As an example, plot (C) in FIG. 4 shows the measured relationship between HTPG and viscosity for each component in the virtual asphalt blend. (It is noted that a measured relationship between HTPG and cut point temperature could be used instead.) Based on the viscosity for each component at the virtual cut point, the HTPG for each component can be determined. In the case of HTPG as a property, it has been determined that weighted linear combinations of HTPG values provides less useful predictions. Instead, weighted combinations of the logs of HTPG values have been found to provide better predictions. Thus, plot (C) shows the correlation between log HTPG values and viscosity. The log HTPG value for each component can be determined from plot (C), as shown in column (8). The values in column (8) can be multiplied by the component weight from column (6) to determine a predicted HTPG value for the asphalt of 59.6° C. A similar prediction for LTPG can be made using plot (D) in FIG. 4 to determine the values shown in column (9). The resulting LTPG prediction for the asphalt fraction is −29.9° C. For comparison, subsequent measurements of the HTPG and LTPG values for the asphalt fraction were 60.7° C. and −29.8° C., respectively. This prediction process can be repeated for other desired properties of an asphalt fraction.

Based on the above, the predicted HTPG and LTPG values for the asphalt fraction differ from the measured values. These residual differences can be reduced by including a fit parameter for each property included in the model. For example, a fit parameter can be associated with property of each crude source included within the model. When a prediction is made for a blended asphalt property, the fit parameters can modify the predicted value based on any systemic differences that occur when a given crude source is used as part of the initial feed for forming a blended asphalt.

ADDITIONAL EMBODIMENTS

Embodiment 1

A method for predicting asphalt properties, comprising: measuring a kinematic viscosity of an asphalt fraction at a temperature of 100° C. to 150° C., the asphalt fraction being formed by separation of a feed containing asphalt components from a plurality of crude sources based on a cut point temperature, the asphalt components being present in the feed in a first set of ratios; determining a virtual cut point for a virtual asphalt blend comprising the asphalt components having a kinematic viscosity that is within a viscosity tolerance of the measured kinematic viscosity, the virtual cut point being determined based on measured kinematic viscosity values for the asphalt components and the first set of ratios for the asphalt components; calculating a second set of ratios corresponding to a virtual composition of the asphalt components in the virtual asphalt blend based on the virtual cut point; calculating one or more properties other than kinematic viscosity for the asphalt fraction based on the second set of ratios for the asphalt components and at least one of the virtual cut point, the measured kinematic viscosity, or the determined kinematic viscosity for the virtual asphalt blend; and modifying the cut point temperature for the separation based on a calculated value for at least one of the one or more properties other than kinematic viscosity.

Embodiment 2

The method of Embodiment 1, further comprising obtaining kinematic viscosity values at a plurality of cut point temperatures for a plurality of asphalt components, each of the plurality of asphalt components corresponding to an asphalt fraction derived from a single crude source at an identified cut point; obtaining values for one or more additional properties for each of the plurality of asphalt components; obtaining values for kinematic viscosity and for the one or more additional properties for a plurality of asphalt fractions comprising asphalt components from two or more crude sources; and constructing a predictive model that correlates a measured viscosity value with values for the one or more additional properties for an asphalt fraction comprising a plurality of asphalt components, the predictive model comprising parameters for the one or more additional properties for each asphalt component that are fit to the obtained values for the plurality of asphalt fractions comprising asphalt components from two or more crude sources.

Embodiment 3

The method of any of the above embodiments, wherein the separation comprises at least one of an atmospheric distillation or a vacuum distillation.

Embodiment 4

The method of any of the above embodiments, wherein modifying the cut point temperature for the separation comprises modifying the cut point temperature based on the calculated value for at least one of the one or more properties being above a threshold value, below a threshold value, or outside of a threshold range.

Embodiment 5

The method of any of the above embodiments, wherein modifying the cut point temperature for the separation comprises modifying the cut point temperature based on a calculated value for at least one of a high temperature performance grade or a low temperature performance grade.

Embodiment 6

The method of any of the above embodiments, wherein calculating the one or more properties comprises calculating a weighted average of asphalt component property values for at least one property based on the second set of ratios.

Embodiment 7

The method of any of the above embodiments, wherein calculating the one or more properties comprises calculating a weighted average of the log of asphalt component property values for at least one property based on the second set of ratios.

Embodiment 8

The method of Embodiment 6 or 7, wherein the calculated weighted average is further based on at least one blending coefficient corresponding to an interaction between two or more crudes sources in the asphalt fraction.

Embodiment 9

The method of any of the above embodiments, wherein measuring the kinematic viscosity comprises measuring the kinematic viscosity of a slip stream withdrawn from the asphalt fraction.

Embodiment 10

The method of any of the above embodiments, wherein the asphalt fraction comprises at least four asphalt components.

Embodiment 11

The method of any of the above embodiments, wherein the viscosity tolerance is 0.05 cSt or less.

Embodiment 12

The method of any of the above embodiments, wherein obtaining values for kinematic viscosity and for the one or more additional properties for a plurality of asphalt fractions comprises obtaining values for asphalt fractions corresponding to a plurality of refineries.

Embodiment 13

The method of any of Embodiments 2-12, wherein constructing the predictive model further comprises fitting a plurality of blending coefficients corresponding to interactions between asphalt components.

Embodiment 14

The method of any of Embodiments 2-13, further comprising updating the fit of at least one parameter in the predictive model based on the measured kinematic viscosity value of the first asphalt fraction.

Embodiment 15

The method of any of Embodiments 2-14, further comprising: measuring values for at least one of the one or more properties of the first asphalt fraction; and updating the fit of at least one parameter in the predictive model based on the measured value for at least one of the one or more properties of the first asphalt fraction.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for predicting asphalt properties, comprising:
separating a feed containing asphalt components from a plurality of crude sources based on a cut point temperature to form at least an asphalt fraction, the asphalt components being present in the feed in a first set of asphalt component weight ratios;
measuring a kinematic viscosity of the asphalt fraction at a temperature of 100° C. to 150° C.;
determining a virtual cut point for a virtual asphalt blend comprising the asphalt components having a kinematic viscosity that is within a viscosity tolerance of the measured kinematic viscosity, the virtual cut point being determined based on the measured kinematic viscosity for the asphalt components and the first set of asphalt component weight ratios for the asphalt components;
calculating a second set of asphalt component weight ratios corresponding to a virtual composition of the asphalt components in the virtual asphalt blend based on the virtual cut point;
calculating one or more properties other than a kinematic viscosity for the asphalt fraction based on the second set of asphalt component weight ratios for the asphalt components and at least one of the virtual cut point, the measured kinematic viscosity, or the determined the virtual cut point for the virtual asphalt blend; and
modifying, based on at least one of the one or more calculated properties, the cut point temperature for the separating the feed containing asphalt components from a plurality of crude sources.

2. The method of claim 1, wherein the separating the feed containing asphalt components from a plurality of crude sources comprises at least one of an atmospheric distillation or a vacuum distillation.

3. The method of claim 1, wherein modifying the cut point temperature for the separating the feed containing asphalt components from a plurality of crude sources comprises modifying the cut point temperature based on the calculated value for at least one of the one or more properties being above a threshold value, below a threshold value, or outside of a threshold range.

4. The method of claim 1, wherein modifying the cut point temperature for the separating the feed containing asphalt components from a plurality of crude sources comprises modifying the cut point temperature based on a calculated value for at least one of a high temperature performance grade or a low temperature performance grade.

5. The method of claim 1, wherein calculating the one or more properties comprises calculating a weighted average of asphalt component property values for at least one property based on the second set of asphalt component weight ratios.

6. The method of claim 5, wherein the calculated weighted average is further based on at least one blending coefficient corresponding to an interaction between two or more crudes sources in the asphalt fraction.

7. The method of claim 1, wherein calculating the one or more properties comprises calculating a weighted average of the log of asphalt component property values for at least one property based on the second set of asphalt component weight ratios.

8. The method of claim 1, wherein measuring the kinematic viscosity comprises measuring the kinematic viscosity of a slip stream withdrawn from the asphalt fraction.

9. The method of claim 1, wherein the asphalt fraction comprises at least four asphalt components.

10. The method of claim 1, the viscosity tolerance is 0.05 cSt or less.

11. A method for predicting asphalt properties, comprising:
obtaining kinematic viscosity values at a plurality of cut point temperatures for a plurality of asphalt components, each of the plurality of asphalt components corresponding to an asphalt fraction derived from a single crude source at an identified cut point;
obtaining values for one or more additional properties for each of the plurality of asphalt components;
obtaining values for kinematic viscosity and for the one or more additional properties for a plurality of asphalt fractions comprising asphalt components from two or more crude sources;
constructing a predictive model that correlates a measured viscosity value with values for the one or more additional properties for an asphalt fraction, the predictive model comprising parameters for the one or more additional properties for each asphalt component that are fit to the obtained values for the one or more additional properties for the plurality of asphalt components;
separating a feed containing at least two asphalt components based on a cut point temperature to form at least a first asphalt fraction, the at least two asphalt components being present in the feed in a first set of asphalt component weight ratios,
measuring a kinematic viscosity of the first asphalt fraction comprising at least two asphalt components at a temperature of 100° C. to 150° C.;
determining a virtual cut point for a virtual asphalt blend having a kinematic viscosity within a viscosity tolerance value of the measured kinematic viscosity for the first asphalt fraction, the virtual cut point being determined based on the measured kinematic viscosity for the at least two asphalt components and the first set of asphalt component weight ratios for the at least two asphalt components;
calculating a second set of asphalt component weight ratios corresponding to a virtual composition of the asphalt components in the virtual asphalt blend based on the virtual cut point;
predicting one or more properties other than a kinematic viscosity for the first asphalt fraction based on the constructed predictive model, the second set of asphalt component weight ratios and at least one of the virtual cut point, the measured kinematic viscosity for the first asphalt fraction, or the determined the virtual cut point for the virtual asphalt blend; and
modifying, based on at least one of the one or more predicted properties, the cut point temperature for the separating the feed containing at least two asphalt components.

12. The method of claim 11, wherein constructing the predictive model further comprises fitting a plurality of blending coefficients corresponding to interactions between asphalt components.

13. The method of claim 11, further comprising updating the fit of at least one parameter in the predictive model based on the measured kinematic viscosity value of the first asphalt fraction.

14. The method of claim 11, further comprising:
   measuring values for at least one of the one or more properties of the first asphalt fraction; and
   updating the fit of at least one parameter in the predictive model based on the measured value for at least one of the one or more properties of the first asphalt fraction.

15. The method of claim 11, wherein obtaining values for kinematic viscosity and for the one or more additional properties for a plurality of asphalt fractions comprises obtaining values for asphalt fractions corresponding to a plurality of refineries.

16. The method of claim 11, wherein modifying the cut point temperature for the separating the feed containing at least two asphalt components comprises modifying the cut point temperature based on the calculated value for at least one of the one or more properties being above a threshold value, below a threshold value, or outside of a threshold range.

17. The method of claim 11, wherein modifying the cut point temperature for the separating the feed containing at least two asphalt components comprises modifying the cut point temperature based on a calculated value for at least one of a high temperature performance grade or a low temperature performance grade.

18. The method of claim 11, wherein measuring the kinematic viscosity comprises measuring the kinematic viscosity of a slip stream withdrawn from the asphalt fraction.

19. The method of claim 11, wherein the viscosity tolerance is 0.05 cSt or less.

* * * * *